United States Patent
Kim et al.

(10) Patent No.: US 6,947,144 B2
(45) Date of Patent: Sep. 20, 2005

(54) VIVO MONITORING METHOD OF TRANSGENIC PLANTS AND SYSTEM USING THE SAME

(75) Inventors: Joo-Kon Kim, Yongin (KR); Byoung-Chull Chung, Pusan (KR); Yong-Joo Park, Taejon (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 0 days.

(21) Appl. No.: 10/257,154

(22) PCT Filed: Apr. 4, 2001

(86) PCT No.: PCT/KR01/00566

§ 371 (c)(1),
(2), (4) Date: Jan. 22, 2003

(87) PCT Pub. No.: WO01/77671

PCT Pub. Date: Oct. 18, 2001

(65) Prior Publication Data

US 2003/0148258 A1 Aug. 7, 2003

(30) Foreign Application Priority Data

Apr. 7, 2000 (KR) .................................. 2000-018104

(51) Int. Cl.⁷ ............................. H01J 65/08; G01J 3/30
(52) U.S. Cl. .................... 356/417; 356/317; 250/459.1
(58) Field of Search ........................ 356/317, 417; 250/458.1, 459.1, 461.1, 461.2

(56) References Cited

U.S. PATENT DOCUMENTS

| | | | | |
|---|---|---|---|---|
| 4,421,772 A | * | 12/1983 | Munck et al. | 426/231 |
| 6,025,485 A | | 2/2000 | Kamb et al. | 536/25.32 |
| 6,573,512 B1 | * | 6/2003 | Lucia et al. | 250/458.1 |

FOREIGN PATENT DOCUMENTS

| | | | | |
|---|---|---|---|---|
| WO | 95/07463 | 3/1995 | | G01N/33/53 |
| WO | 97/41228 | 11/1997 | | C12N/15/12 |
| WO | 98/45704 | 10/1998 | | G01N/33/53 |
| WO | WO 99/32876 | * | 7/1999 | |

* cited by examiner

Primary Examiner—Zandra V. Smith
(74) Attorney, Agent, or Firm—Darby & Darby

(57) ABSTRACT

The present invention relates to a method for visualizing GFP expression in callus, various tissue and organ of the transgenic plants as image and system using the same. The said method needs no other additional genetic product, substrate or cofactor and can detect very simply and quickly GFP expression by using the said system of the present invention consisting of a CCD camera, a light source, band-pass filter and data processing computer, so it provides many advantages for selection of transgenic seeds, for studying of gene expression in the tissue or organ of plants, or for studying of specificity of each development step.

4 Claims, 6 Drawing Sheets

VIVO MONITORING METHOD OF TRANSGENIC PLANTS AND SYSTEM USING THE SAME

TECHNICAL FIELD

The present invention relates to a method and system for monitoring the transformation of plants. More particularly, the present invention relates to a fluorometry method and system for the visualization of the in vivo expression of a green fluorescent protein gene tagged to an exogenous gene of interest, thereby enabling the plants to be determined as to whether they are transformed with the exogenous gene or not.

BACKGROUND ART

Reporter proteins are usually used as markers for visualizing in vivo gene expression and protein translocation in eucaryotic and prokaryotic organisms. The most widely used reporter proteins in plants may be exemplified by β-glucuronidase (GUS) and luciferase (LUC). Particularly, GUS is a prevalent visualization marker in the plant cell biology (Jefferson R A, et al., (1987), EMBO J., 6:3901–3907). However, histochemical GUC analysis is not suitable for the direct visual selection of transgenic plants per se because it requires the destruction of plant tissues. As for LUC, its in vivo synthesis can be detected; however, an external substrate, that is luciferin, is required for the detection of LUC. In addition, LUC has the disadvantage of emitting a low intensity of light (Ow D W et al., Science 234:856–859).

Recently, it has been reported that the green fluorescent protein (GFP) of jellyfish Aquorea Victoria can be utilized as a sensitive reporter for in vivo gene expression (Chalfie M., et al., 1994, Science 263:802–805). Even though requiring no external factors, the detection of the fluorescence generated from an isolated GFP is possible only with near infrared (386 nm) or blue light (475 nm). However, the fluorescence of the GFP can be observed under visible light in room conditions (Chalfie M., et al., 1994, Science 263:802–805; Delagrave S., et al., 1995, Bio/Technology 13:151–154; Heim R, et al., 1994, Proc Nat'l, Acad Sci. USA, 94:2122–2127). Further, GFP model is very advantageous in that it retains fluorescence even when being expressed in heterologous biosystems, such as E. coli, yeast, Drosophila, insects, mammals, etc. (Brand A 1995, TIG 11:324–325; Chalfie M., et al., 1994, Science 263:802–805; Cubitt A B, et al., 1995, TIBS 20:448–455; Davis S J, et al., 1998, Plant Mol. Biol. 36:521–528; Delagrave S, et al., 1995, Bio/Technology 13:151–154; Haseloff J., et al., 1997, Proc. Nat'l Acad. Sci. USA, 94:2122–2127; Rosario R., et al., 1995, Curr. Biol. 5:635–642; Wang S X et al., 1994, Nature 369:400–403).

Bioassays for gene expression using fluorescence are very useful for monitoring the transformation and growth of plants. Because of plant tissues' being composed of highly reflective cell walls and aqueous cytoplasm containing various autofluorescent and light-scattering materials, it is difficult to directly observe the exogenous fluorescence of proteins introduced into plant tissues under a fluorescent optical microscope (Haseloff J. et al., 1998, Green fluorescent protein: Properties, applications, and protocols. Chalfie M., Kain S., Eds., Wiley-Liss, New York, pp 191–242). For this reason, the use of GFP as a marker for the selection of transgenic plants under direct visual conditions has not yet been reported.

DISCLOSURE OF THE INVENTION

Leading to the present invention, the intensive and thorough research on the identification of transgenic plants, conducted by the present inventors, resulted in the finding that, when a filtered light beam which can excite GFP is projected to a plant sample of interest, light is emitted from the plant sample and, if filtered through a green bandpass filter, can be analyzed for the expression of GFP by use of a CCD (charge-coupled device) camera imaging system.

Therefore, it is an object of the present invention to provide a method for monitoring the transformation of plants using GFP as a reporter.

It is another object of the present invention to provide a CCD imaging system for visualizing the in vivo expression of GFP.

In an aspect of the present invention, there is provided a fluorometry method for monitoring the transformation of plants based on the in vivo expression of a heterologous green fluorescent protein, comprising the steps: projecting excitation light from a light source through a blue bandpass filter onto a plant sample at an angle of 45°, said blue bandpass filter passing light ranging, in wavelength, from 470 to 490, said excitation light having a wavelength of around 488 nm with a peak at 480 nm; detecting light generated from the plant sample by use of a charge coupled device color video camera equipped with a zoom lens, which is positioned on the axis vertical to the plane of the sample, said light passing through a green bandpass filter which passes light ranging, in wavelength, from 500 to 550 nm before arriving at said zoom lens, so as to have a wavelength of around 509 nm, and photographing the image of the plant sample on the basis of the light generated from the plant sample; and processing the image in a computer to determine whether the plant sample is transgenic or not.

In another aspect of the present invention, there is provided a system for monitoring the transformation of plants on the basis of the in vivo expression of a heterologous green fluorescent protein, utilizing the method.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

The present invention pertains to the non-invasive visualization of the fluorescence of the GFP expressed in transgenic plant tissues or organs, including rice calluses grown in light-illuminated and shielded conditions, with the aid of a fluorometry system comprising a CCD camera, a light source, bandpass filters, and a computer for processing data, in accordance with the present invention.

In the present invention, a bioassay using fluorescence of GFP is provided for monitoring the transformation of plants. Fluorometry for detecting in vivo fluorescence of the GFP expressed in transformed plants and a system therefor are described in connection with the accompanying drawings. Before the present method and system for monitoring the transformation of plants is disclosed or described, it is to be understood that the terminology used therein is for the purpose of describing particular embodiments only and is not intended to be limiting.

The application of the preferred embodiments of the present invention is best understood with reference to the accompanying drawings.

Figure 3:
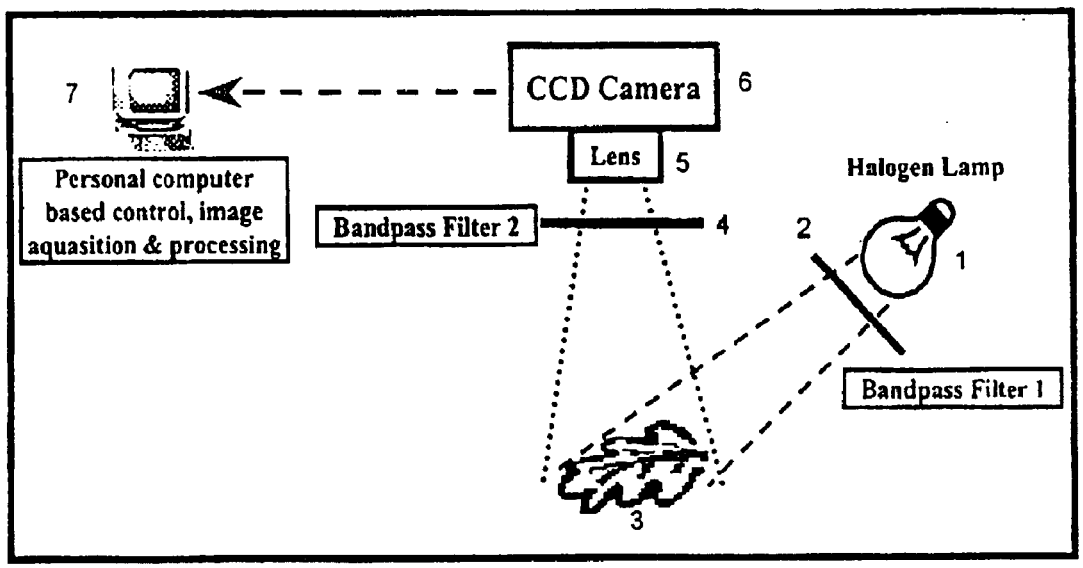
FIG. 3 is an illustration of a CCD imaging system for GFP.

Referring to FIG. 3, there is shown the application of a digital video imaging system to a leaf to identify whether the plant is transgenic or not by detecting the fluorescence emitted therefrom. As a light source, there is used a 250W halogen lamp 1 which generates excitation light. In front of the halogen lamp 1 is positioned a blue bandpass filter 2 (Edmund, USA) through which only the light with a wavelength in the range of 470 to 490 nm (max light wave 480 nm) can pass, because light with a wavelength of around 488 nm can excite GFP. Light beams are projected to a plant sample 3 at an angle of about 45° to the axis vertical to the plane of the plant sample. In one embodiment of the present invention, the illumination area was set to be 4 cm$^2$ at a maximum photon flux density (PFD) of 2 $\mu$mole m$^{-2}$s$^{-1}$. When the filtered light is irradiated to the sample, the GFP expressed in vivo is excited and emits fluorescent light. Using this fluorescence generated from the sample, the image of the sample can be visualized in a photograph. In this regard, a high-resolution CCD color video camera 6 equipped with a zoom lens 5 is positioned on the axis vertical to the plane of the sample to take a photograph of the sample while focusing on a certain area of the sample with the zoom lens. Because the light emitted from the GFP has a wavelength of about 509 nm, a bandpass filter 4 for passing the green light ranging in wavelength from 500 to 550 nm is established in front of the CCD camera to pass the green fluorescent light only. Then, images photographed by the CCD are sent to a computer in which the image data are collected, stored and processed.

Figure 4:
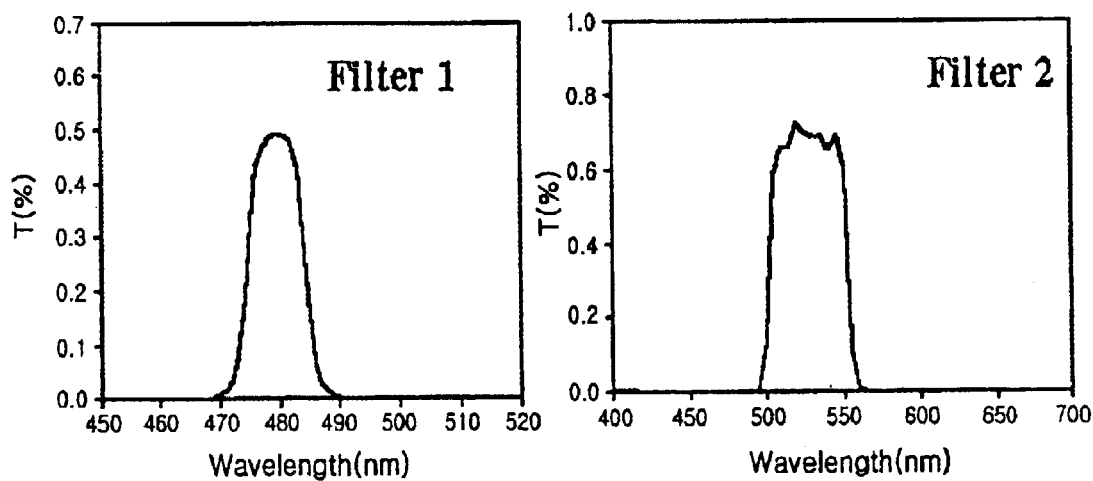
FIG. 4 shows profiles of light beams which pass through bandpass filters established in front of a light source and a CCD lens, respectively.

With reference to FIG. 4, there are shown transmittances of the light having peaks at 480 nm and 510 nm, which are filtered through the blue bandpass filter 2 and the green bandpass filter 4, respectively.

Figure 8:
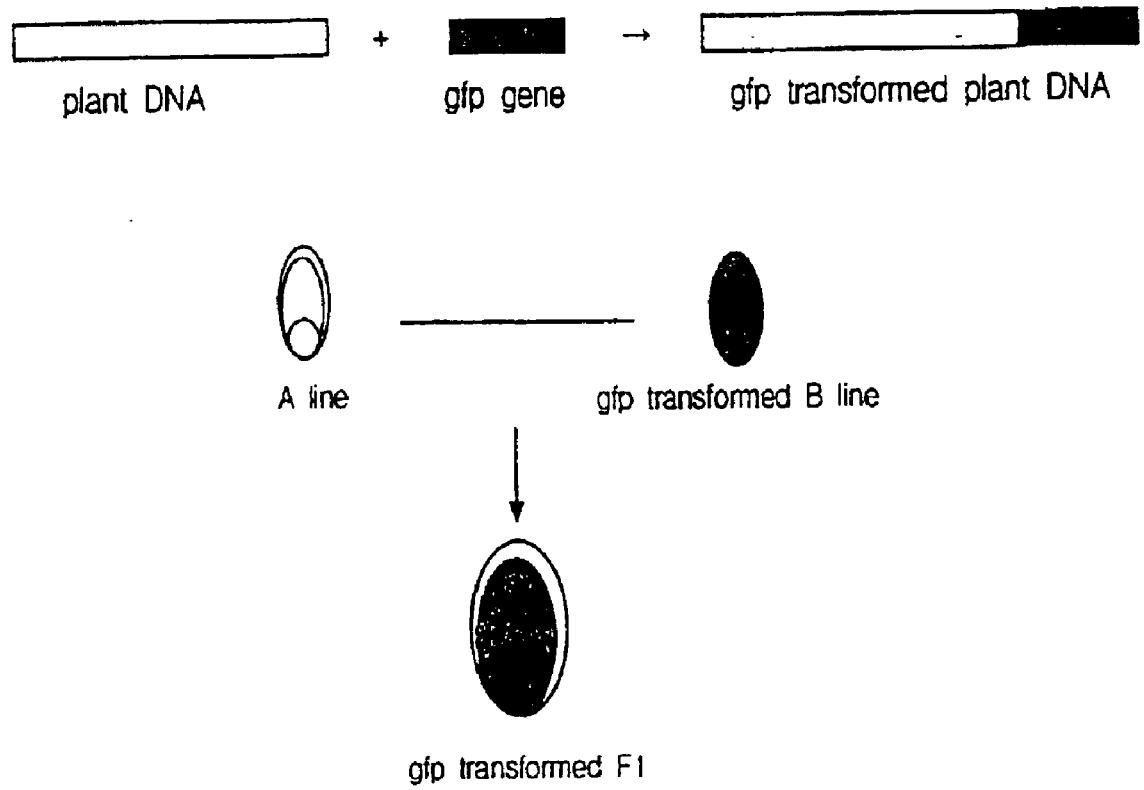
FIG. 8 is a schematic diagram illustrating the tagging of a gfp gene to a gene of interest and the crossing of a transformed line with a wild type line.
Figure 9:
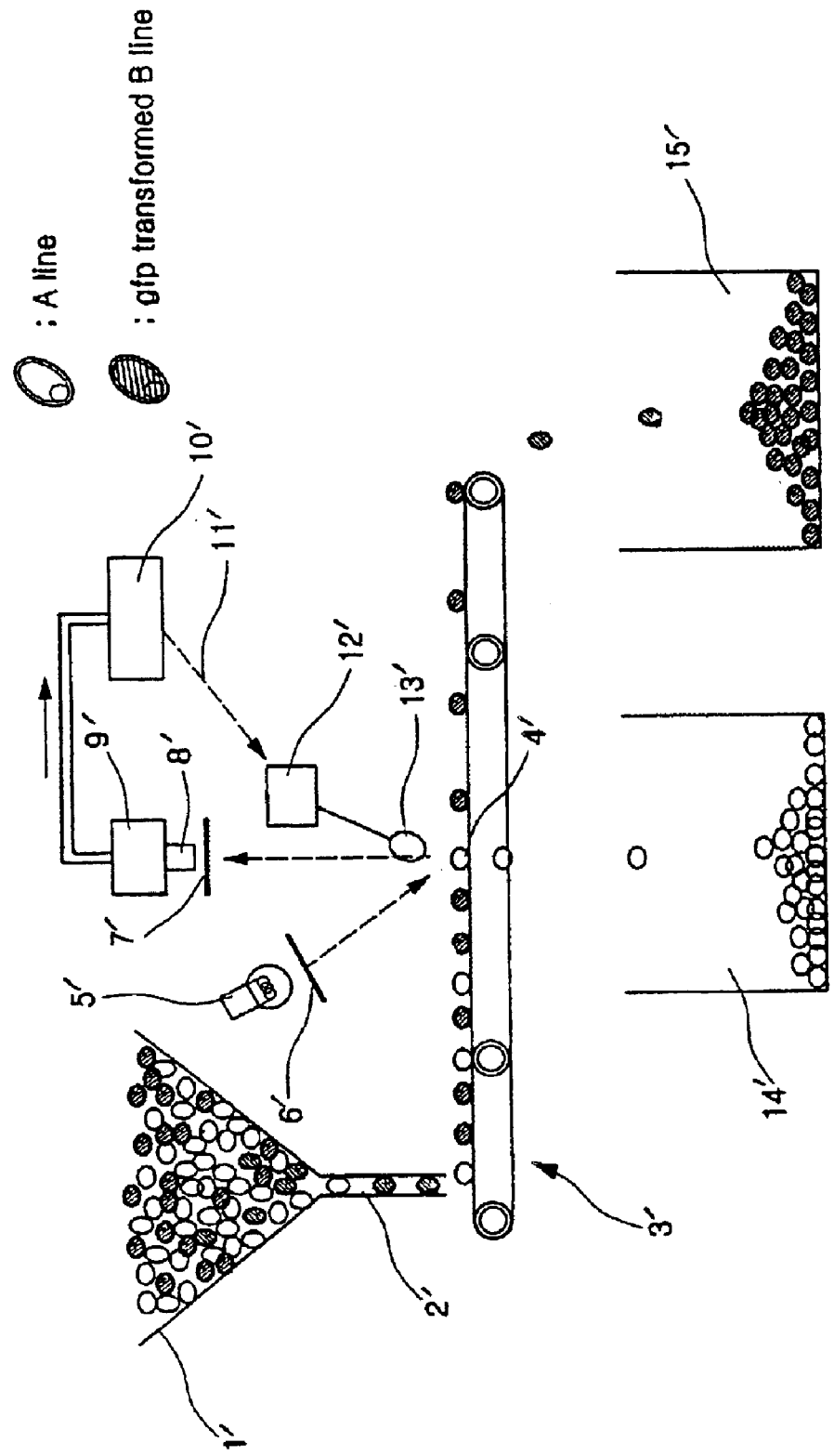
FIG. 9 shows a seed sorting machine useful to carry out an embodiment of the present invention.

FIG. 9 shows a sorting machine for separating seeds transformed with a gfp gene from those that lack the exogenous gfp gene by taking advantage of the fluorescence resulting from the in vivo expression of GFP. Seeds having an exogenous gene tagged with a gfp gene can be obtained as illustrated in FIG. 8. A gene which provides a characteristic of interest is combined with a gfp gene to give a hybrid DNA, followed by the transduction of the hybrid DNA into a plant cell line A. Then, the plant seed harboring the gene of interest is crossed with a cell line B which does not contain the exogenous gene to produce a gfp-transformed progeny F1. Returning to FIG. 9, harvested seeds 4' are put in a seed collector 1' and dropped onto a conveyor belt 3' through a seed path 2' which restricts the size of the seeds 4'. The seeds 4' arrived on the conveyor belt 3' are moved as the conveyor belt 3' runs. During the migration on the conveyor belt 3', the seeds 4' pass by a fluorometry system and a seed sorter. At this time, light is irradiated from a light source 5' to a seed 4'. In this connection, the light generated from the light source 5' is filtered through a bandpass filter 6' so that the wavelengths of the light illuminated on the seed 4' fall within a particular range. When being irradiated with a light beam within a particular wavelength range, the seed 4' fluoresces if it is transformed with the gene of interest tagged with the gfp gene. Then, the fluorescence is detected by a CCD camera 9' equipped with a zoom lens 8', which is established to receive the fluorescent light in the direction perpendicular to the migration direction of the conveyor belt 3'. Before entering the zoom lens 8', the fluorescence light generated from the seed 4' goes through a bandpass filter 7' which passes the light in the wavelength range of GFP fluorescence only. An image of the seed is visualized in the CCD camera 9' from which the image information is transmitted to the data processor 10' in which the information is processed to determine whether the seed is transgenic or not. A signal 11' concerning the determination is generated from the processor 10' and sent to a controller 12'. According to the signal, the controller 12' operates a seed sorter 13' in ON/OFF states alternatively. For example, when the seed 4' does not show fluorescence, the seed sorter 13' is let to enter an ON state to select the seed 4' into a non-transgenic seed collector 14'. On the other hand, when the fluorescence is detected from the seed 4', the operation of the seed sorter 13' is ceased so that the seed 4' is migrated, along the conveyor belt 3', to a transgenic seed collector 15'. Alternatively, the seed sorter 13' may be operated in such a way as to select transgenic seeds only. In this case, non-transgenic seeds 4' are let to migrate to the end of the belt 3'. Therefore, the seed sorting machine of the present invention allows the purity of the transgenic progeny F1 and the line B to be assayed, as well as enabling the selection of the transgenic F1 progeny.

The method for detecting the fluorescence resulting from GFP expression of the present invention enjoys the advantages of being performed quickly and with ease and requiring no additional factors, including gene products, substrates, subsidiary factors, etc. For example, it is possible to determine whether a protein of interest is expressed in vivo with the aid of neither enzymes nor antibodies. More recently, there has been suggested the potential application of GFP as a visualization marker in tobacco plants (Molinier J. et al., 2000, Plant Cell Reports 19:219–223). However, it was very difficult to take a photograph of a green image from old leaves in which vacuoles are well developed.

Based on the in vivo expression of GFP, the visualization method of the present invention is anticipated to make great contribution to the study of gene expression in various plant tissues and organs and of developmental traits, as well as the selection of transgenic seeds.

A better understanding of the present invention may be obtained in light of the following examples which are set forth to illustrate, but are not to be construed to limit the present invention.

EXAMPLE 1

Construction of Vector

Figure 1:
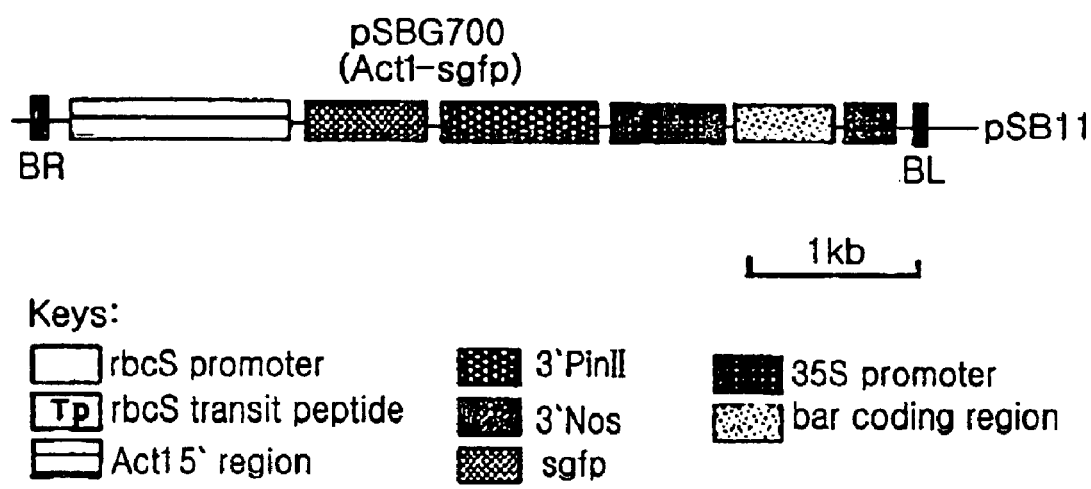
FIG. 1 is a schematic diagram showing the plasmid pSBG700.

After being digested with BamHI and NcoI, a rice-derived Act1 promoter (McElroy D. et al., 1991, Mol. Gen. Genet. 231:150–160 was inserted into a BamHI/NcoI-linearized pBluescript plasmid containing an sgfp gene (Kohler R H. et al., 1997, Plant J. 11:613–621). Treatment of the resulting recombinant plasmid with BamHI and NotI extracted an Act1 promoter-sgfp fragment. This DNA fragment was ligated to a BamHI/NotI-linearized pSB105 that contained potato proteinase inhibitor II terminator/35S promoter/bar/ nopaline synthase terminator to construct a recombinant plasmid, named pSBG700, as illustrated in FIG. 1. Using the tripatental mating method disclosed in Komari T., et al., 1996, Plant J. 19:165–174), Agrobacterium tumefacience LBA4404 was transformed with the plasmid pSBG700.

EXAMPLE 2

Transformation of Rice

A wild-type rice seed (*Oryza sativa* cv. Nakdong) and a rice seed transformed with an agfp gene (Jang et al., 1999, Molecular breeding 5:453–461) were treated with 70% ethanol for 1 hour and then with 10% sodium hypochlorite for 15 min. After being washed five times with sterile water, the seeds were sowed in test tubes containing MS salt (Murashige T., Skoog F., 1962, Physiol. Plant, 15:473–497), sucrose 30 g/l, and bactoagar 8 g/l. Subsequently, the test tubes were incubated in a growth chamber which was adjusted to a temperature of 25° C. with a PFD maintained at 100 $\mu$mol m$^{-2}$s$^{-1}$. Under light-illuminated and shielded conditions, the seeds were let to grow for 16 hours and 8 hours, respectively. The seeds were germinated to white plants in the test tubes in the dark. In petri dishes containing MS salt, glucose 30 g/l, 2,4-D 2 mg/l, and bactoagar 8 g/l, calluses were induced from the white sprouts and grown at 25° C. in the growth chamber under the controlled conditions.

In order to achieve transduction by use of Agrobacterium, as many as 200 seeds (*Oryza sativa* cv. Nakdong) were removed of their hulls and then treated with 70% ethanol for 1 min with gentle agitation. Following decantation of the ethanol, the seeds were sterilized again in 10 ml of 20% clorax for 1 min with gentle agitation and then washed with sterile water. The induction of calluses, and the selection of transformed calluses subsequent to the co-cultivation thereof together with Agrobacterium were performed in the same manner as disclosed (Hiei Y. et al., 1994, Plant J. 6:271–282) except that ?phosphyinotrysin was added at amounts of 7 mg/l and 4 mg/l to the selection medium and the regeneration medium, respectively.

EXAMPLE 3

GFP Fluorometry

To determine the excitation and emission spectra of the GFP that the transgenic plants produced, water-soluble proteins were extracted from leaves of the transgenic rice which had been grown for three months.

To this end, first, sliced leaves were homogenized in an extraction buffer (20 mM Tris-HCl, pH 8.0, 10 mM EDTA, 30 mM NaCl, 2 mM phenylmethanesulfonyl fluoride). After the centrifugation of the homogenate at 12,000×g for 10 min, a portion of the supernatant thus obtained was added to the extraction buffer to make a final volume of 1 ml. Using an assay kit (Bio-Rad) according to manufacturer's instruction, water-soluble proteins were quantitatively analyzed with bovine serum albumin serving as a control.

At room temperature, a quantitative measurement was made of the GFP fluorescence of cell extracts with the aid of an F-450 fluorometer (Hitachi, Japan) in 10 mm/10 mm cuvettes. After passing through the excitation and emission monochromator used in the present invention, the light had a bandpass of 5 nm. As for the emission spectrum, it was read at a fixed excitation ultrahigh wavelength (488) and a fixed emission high wavelength (510 nm).

Figure 2:
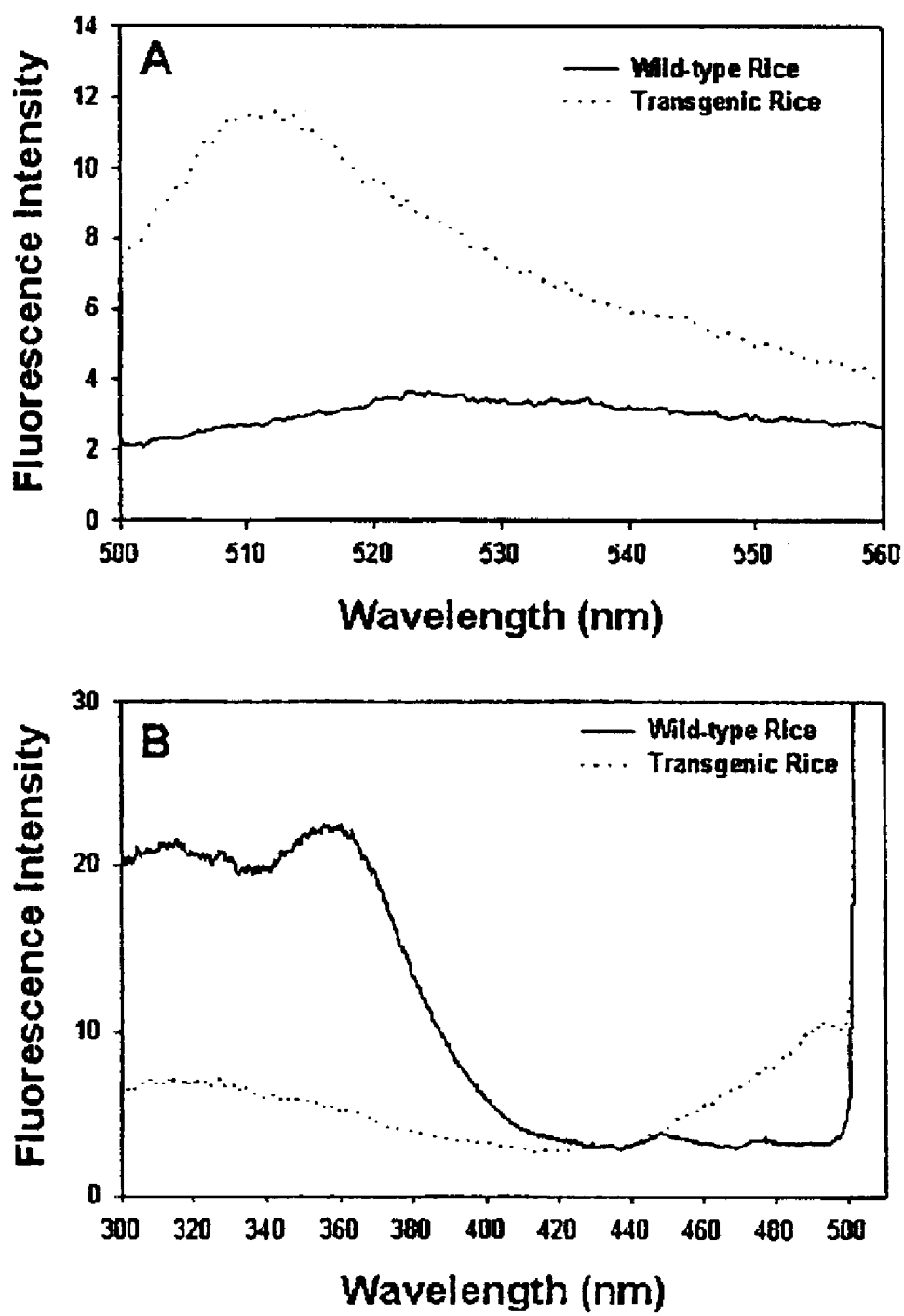
FIG. 2 shows excitation (A) and emission (B) spectra of GFP in wild type and transgenic rice leaves.

Results of the fluorometry are given in FIG. 2. As seen in FIG. 2, the spectrum of the transgenic rice is different from that of the wild-type rice: the blue-green excitation light (480 nm) of GFP was found to cause a green fluorescence peak at around 510 nm. Accordingly, it was demonstrated that the distinctive green fluorescence of the transgenic seed was originated from the product of the sgfp gene.

EXAMPLE 4

Visualization of Image from GFP Fluorescence

It is certain that, if the expression of a gene of interest is visualized from a live body per se, great advances will be made possible in molecular biological and biochemical research for gene expression, signal transduction, cell division, and protein location.

In order to monitor gene expression in a rice plant, a jellyfish gene encoding GFP was used as a marker. To this end, the GFP gene was attached to an Act1 promoter. After being transformed with a recombinant plasmid harboring the GFP gene downstream of the Act1 promoter, calluses were grown to sprout under light, and finally, seeds were obtained. From transgenic plants in each developmental stage, the fluorescence resulting from the expression of GFP was detected. Image data from the transgenic plants was compared with that from wild type plants.

A digital video imaging system comprising a halogen lamp, bandpass filters, a CCD camera equipped with a zoom lens, and a computer was arranged as shown in FIG. 3 to take images of plants by use of the GFP fluorescence therefrom. The light generated from a 250W halogen lamp was passed through a blue bandpass filter (Edmund, USA) to produce excitation light having a peak at 480 nm. This filtered light was projected to a plant sample at an angle of 45° to the axis vertical to the horizontal plane of the sample. The illumination area was set to be 4 cm$^2$ at a maximum photon flux density (PFD) of 2 $\mu$mole m$^{-2}$s$^{-1}$. A high-resolution CCD color video camera (Roper Scientific Inc., USA, Model CoolSNAP) equipped with a zoom lens (Nikon, Japan) was positioned on the axis vertical to the plane of the sample to take a photograph of the sample while focusing on a certain area of 20 mm×20 mm of the sample by use of the zoom lens. A bandpass filter for passing green light was established in front of the CCD camera to pass only the green fluorescent light having a peak at 510 nm. The light passing through the blue bandpass filter and the green bandpass filter had peaks at 480 nm and 510 nm, respectively, as shown in FIG. 4. The images taken by the CCD camera were transmitted through an interface board (Roper Scientific Inc., USA) to a personal computer (Pentium III CPU at 500 MHz, Intel Corp., USA) and the image data was stored therein. Image results are shown in FIGS. 5 to 7.

Figure 5:
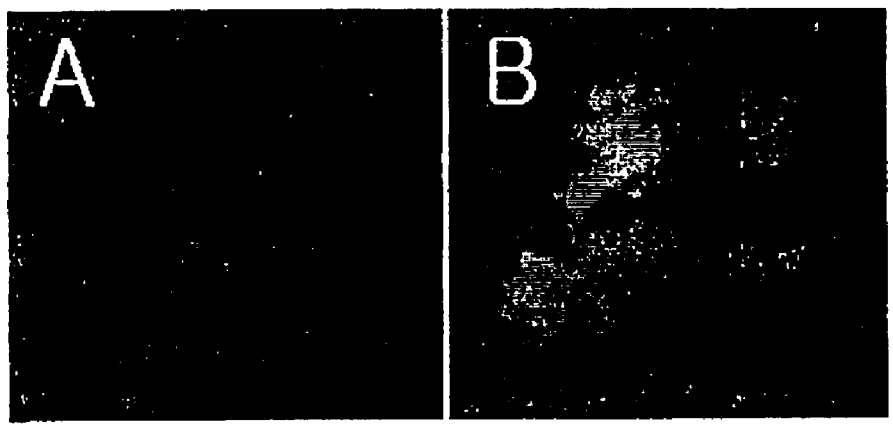
FIG. 5 shows fluorographs visualizing the expression of GFP in a wild type rice callus (A) and a transgenic rice callus (B).

Referring to FIG. 5, there are two fluorographs of calluses which were of wild type (A) and transformed with a GFP gene (B), respectively. As seen in these fluorographs, the characteristic green fluorescence observed in the transformed callus is found to result from the expression of GFP in the callus because no fluorescence was observed in the wild type callus. In detecting GFP fluorescence, the red autofluorescence of chlorophyll usually acts as an inhibitory factor. However, the system comprising suitable bandpass filters, a sensitive CCD camera, and a relatively intense light beam could overcome the barrier.

Figure 6:
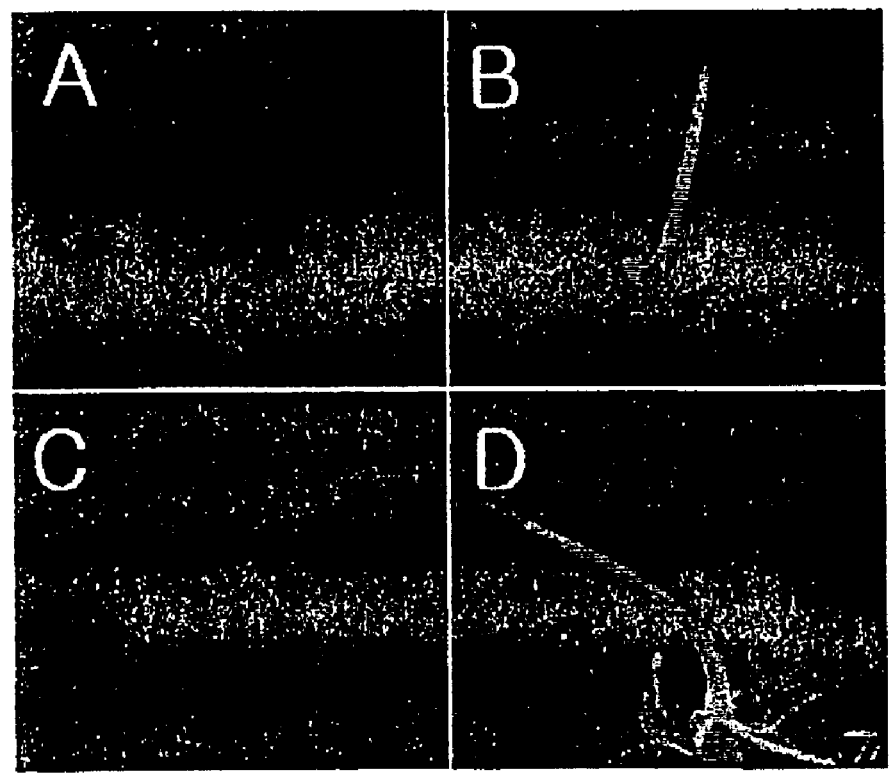
FIG. 6 shows fluorographs visualizing the expression of GFP in a wild-type, white rice sprout (A), a transgenic, white rice sprout (B), a wild-type, green rice sprout (C), and a transgenic, green rice sprout (D).

With reference to FIG. 6, fluorographs of rice sprouts are shown. Wild type sprouts exhibited no fluorescence (left panel A and C) while bright green fluorescence was detected from the whole organs of transgenic white and green sprouts (right panel B and D).

Figure 7:
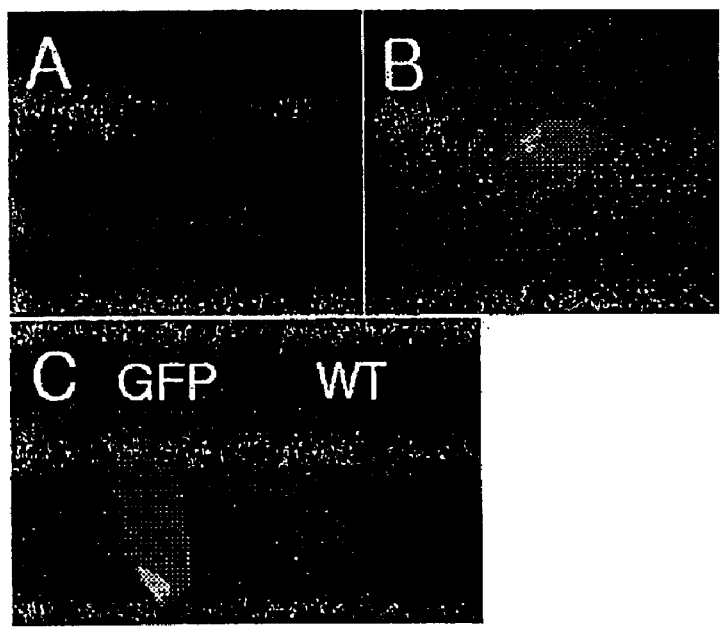
FIG. 7 shows fluorographs visualizing the expression of GFP in a wild-type, unshelled rice seed (A), a transgenic, unshelled rice seed (B), and a transgenic, shelled rice seed (C).

FIG. 7 shows fluorographs taken from rice seeds which are a wild type (A) and transgenic (B and C). No fluorescence was observed from the wild type rice seed (A). On the other hand, the expression of GFP in transgenic rice seeds was detected whether they were shelled or not (B and C).

INDUSTRIAL APPLICABILITY

As described hereinbefore, the method and system of the present invention requires no additional gene products, substrates, nor subsidiary factors in visualizing the expression of GFP in various plant organs and tissues, including calluses, sprouts, and seeds. In addition, the method and system of the present invention can detect in vivo GFP expression very quickly and easily, making great contribution to research into gene expression in various plant tissues and organs, and developmental traits, as well as the selection of transgenic seeds.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A fluorometry method for monitoring the transformation of plants, comprising the steps:

projecting excitation light from a light source through a blue bandpass filter onto a plant sample at an angle of 45°, said blue bandpass filter passing light ranging, in wavelength, from 470 to 490 nm, said excitation light having a wavelength of around 488 rim with a peak at 480 nm;

detecting light generated from the plant sample by use of a charge coupled device color video camera equipped with a zoom lens, which is positioned on the axis vertical to the plane of the sample, said light passing through a green bandpass filter which passes light ranging, in wavelength, from 500 to 550 nm before arriving at said zoom lens, so as to have a wavelength of around 509 nm, and photographing the image of the plant sample on the basis of the light generated from the plant sample; and processing the image in a computer to determine whether the plant sample is transgenic or not based on the in vivo expression of a heterologous green fluorescent protein.

2. A system for monitoring the transformation of plants on the basis of the in vivo expression of a heterologous green fluorescent protein, utilizing the method of claim 1, wherein the system comprises:

a container to collect plant samples;

a device that moves the plant sample;

a device that performs the method of claim 1;

a device that sorts the plant samples based on the result of the method performed by the device that performs the method of claim 1, wherein the result may be used to determine if a plant sample exhibits green fluorescent protein-induced fluorescence; another container that stores the separated plant samples in separate holding areas after sorting.

3. The method of claim 1, wherein the plant sample is a seed.

4. The system of claim 2, wherein the plant sample is a seed.

* * * * *

UNITED STATES PATENT AND TRADEMARK OFFICE
CERTIFICATE OF CORRECTION

PATENT NO. : 6,947,144 B2  
DATED : September 20, 2005  
INVENTOR(S) : Choon-Hwan Lee It is certified that error appears in the above-identified patent and that said Letters Patent is hereby corrected as shown below:

<u>Title page,</u>
Item [75], Inventors, add -- Choon-Hwan Lee, Pusan-City, Korea --.

Signed and Sealed this

Thirteenth Day of December, 2005

JON W. DUDAS
*Director of the United States Patent and Trademark Office*